United States Patent [19]

Yamada et al.

[11] Patent Number: 5,453,864
[45] Date of Patent: Sep. 26, 1995

[54] LIQUID CRYSTAL ELEMENT AND ELECTRONIC APPARATUS

[75] Inventors: Shuhei Yamada; Nobutaka Suzuki; Masahiro Kuroiwa, all of Suwa, Japan

[73] Assignee: Seiko Epson Corporation, Tokyo, Japan

[21] Appl. No.: 248,266

[22] Filed: May 24, 1994

Related U.S. Application Data

[63] Continuation-in-part of Ser. No. 652,818, Feb. 8, 1991, Pat. No. 5,314,640.

[30] Foreign Application Priority Data

| Feb. 16, 1990 | [JP] | Japan | 2-35692 |
| Mar. 7, 1990 | [JP] | Japan | 2-55570 |
| Apr. 12, 1990 | [JP] | Japan | 2-96916 |
| Jun. 5, 1990 | [JP] | Japan | 2-146766 |
| Jun. 6, 1990 | [JP] | Japan | 2-148095 |
| Oct. 20, 1990 | [JP] | Japan | 2-288006 |

[51] Int. Cl.⁶ .............. G02F 1/13; C09K 19/06; C09K 19/12
[52] U.S. Cl. .............. 359/103; 252/299.6; 252/299.66
[58] Field of Search .............. 252/299.6, 299.66; 359/103

[56] References Cited

U.S. PATENT DOCUMENTS

| 4,003,844 | 1/1977 | Sorkin | 359/96 |
| 4,705,870 | 11/1987 | Takatsu et al. | 549/369 |
| 4,705,905 | 11/1987 | Takatsu et al. | 585/25 |
| 4,713,468 | 12/1987 | Takatsu et al. | 558/411 |
| 4,726,910 | 2/1988 | Takatsu et al. | 252/299.5 |
| 4,726,911 | 2/1988 | Krause et al. | 252/299.61 |
| 4,797,228 | 1/1989 | Goto et al. | 252/299.63 |
| 4,820,878 | 4/1989 | Takatsu et al. | 568/659 |
| 4,839,091 | 6/1989 | Goto et al. | 252/299.63 |
| 4,853,152 | 8/1989 | Goto | 252/299.63 |
| 4,883,609 | 11/1989 | Yamada | 252/299.61 |
| 4,908,152 | 3/1990 | Goto | 252/299.63 |
| 5,068,053 | 11/1991 | Reiffenrath et al. | 252/299.61 |

FOREIGN PATENT DOCUMENTS

| 377516 | 7/1990 | European Pat. Off. . |
| 2504641 | 8/1976 | Germany . |
| 3906038 | 9/1989 | Germany . |
| 155142 | 8/1985 | Japan . |

OTHER PUBLICATIONS

Gray, et al., "Mesomorphic Transition Temperatures . . . ", *Mol. Cryst. Lig. Crst.*, 1976, vol. 37, pp. 213–231.

Fieser, et al. *Organic Chemistry* 3rd Edition (1956) pp. 86–87.

*Primary Examiner*—C. Harris
*Attorney, Agent, or Firm*—Stroock & Stroock & Lavan

[57] ABSTRACT

A liquid crystal display element having flexible substrates, wherein the liquid crystal material disposed between the flexible substrates contains a tolan derivative represented by the general formula:

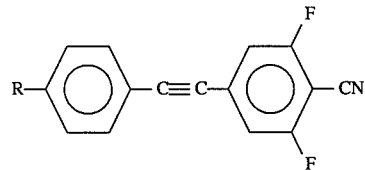

where R is a straight chain alkyl group having 1–10 carbon atoms.

19 Claims, 4 Drawing Sheets

LIQUID CRYSTAL ELEMENT AND ELECTRONIC APPARATUS

CROSS-REFERENCE TO RELATED APPLICATIONS

This is a Continuation-In-Part Application of co-pending U.S. patent application Ser. No. 07/652,818 filed on Feb. 8, 1991, U.S. Pat. No. 5,314,640 the contents of which are incorporated herein by reference.

BACKGROUND OF THE INVENTION

This invention relates generally to liquid crystal cells and more specifically to liquid crystal display (LCD) cells having a flexible substrate formed of materials such as plastics, polymers and the like and to electronic apparati having such a liquid crystal element installed therein.

There has been an increasing demand for plastic film panel (PFP) liquid crystal cells having a flexible substrate formed from materials such as plastics, rather than glass, to be used as display elements for pagers, portable telephones and the like. Such liquid crystal cells are generally light, are not easily broken, and are therefore more transportable. Liquid crystal cells having a flexible substrate have attracted attention as display elements and are sought to replace cells using glass substrates since increased portability is attained due to the features of lightness and unbreakability of the liquid crystal display element. Thus, more reliable liquid crystal cells having flexible substrates are strongly desired. As a result, there has been a great demand that the display mode be changed from a twist nematic (TN) type to a supertwist nematic (STN) type having greater display quality.

Although liquid crystal display cells having flexible substrates have the above-described beneficial features, they also have problems compared with liquid crystal cells which use normal, inorganic glass as a substrate. The problems of liquid crystal cells having flexible substances are as follows: (1) since heat resistance temperature is low, for example, about 150° C., a low temperature manufacturing process must be employed. Therefore, manufacturing conditions and selection of materials different from glass cells are required; (2) since organic substrates typically have inferior resistance to chemicals or solvents compared to glass substrates, the surface of the substrate, display electrodes and the like are more likely to be damaged during stress involving the application of an acid or alkali material such as steps in which the electrode pattern is formed; and (3) since organic materials such as PFP have inferior resistance to the atmosphere, it is easy for gas such as oxygen or other vapors to enter the liquid crystal layer, causing gas bubbles to be generated.

Therefore, the use of flexible substrates for liquid crystal display cells imposes significant limitations on the manufacturing process and materials which constitute the liquid crystal element. Furthermore, reliability matching that of a glass cell has not yet been achieved.

Ordinarily, reliable liquid crystal materials commonly sealed into glass liquid crystal cells have a skeleton such as phenylcyclohexane or biphenyl (hereinafter referred to as "PCH-type liquid crystal material" and "biphenyl-type liquid crystal material", respectively). PCH-type liquid crystal material and biphenyl-type liquid crystal material were included in liquid crystal cells having a glass substrate. An environmental resistance test, including exposure to high temperatures, was conducted and no problems occurred in the liquid crystal cell. However, when these same liquid crystal materials were used in a liquid crystal cell having flexible organic substrates, it was found that the amount of electric current greatly increased over time, and orientation irregularities were observed, thereby deteriorating the quality of the display considerably.

Accordingly, it is desirable to provide a liquid crystal display device having a flexible substrate, which device has a high quality of display as well as exhibiting lightness, unbreakability and portability.

SUMMARY OF THE INVENTION

Generally speaking, in accordance with the invention, a liquid crystal cell having a flexible substrate formed of organic material such as polymers, resins and thermoplastics, is provided. The liquid crystal composition disposed within the cell and against the flexible substrate contains a tolan derivative represented by the general formula:

where R is a straight chain alkyl group having from 1 to 10 carbon atoms. The liquid crystal cell preferably also includes at least one of an ester compound of a cyclohexane carboxylic acid phenyl ester having negative (n-type) induced anisotropy represented by the general formula:

where R and R' are straight chain alkyl groups having from 1–10 carbon atoms, and a benzoic acid phenyl ester having positive (p-type) induced anisotropy represented by the general formula:

where R is a straight chain alkyl group having from 1–10 carbon atoms. Such a liquid crystal cell will have acceptable environmental resistance and high display qualities. The tolan derivative is preferably included in an amount between about 2 to 25 weight percent based on a total weight of the liquid crystal composition.

Accordingly, it is an object of this invention to provide a liquid crystal display device including a flexible substrate having improved environmental resistance and high display qualities.

Another object of the invention is to provide a liquid crystal composition that is compatible with organic substrates.

Still another object of the invention is to provide electronic apparati having improved environmental resistance.

Yet another object of the invention is to provide a light weight and portable liquid crystal display.

Still other objects and advantages of the invention will in part be obvious and will in part be apparent from the specification.

The invention accordingly comprises an apparatus embodying features of construction, combination of elements and arrangement of parts, and a composition of matter possessing the characteristics, properties and the relation of constituents which are to effect such elements, all as exemplified in the detailed disclosure hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

A liquid crystal display element or cell is formed with upper and lower spaced apart flexible substrates and a liquid crystal composition disposed between the flexible substrates. The substrates are preferably formed of organic material such as thermoplastics, resins and polymers to provide lightness, durability and portability. In order to provide acceptable compatibility with plastic substrates, the liquid crystal composition preferably contains a tolan derivative and an estertype liquid crystal material. This provides for a liquid crystal display device having the properties of high environmental resistance and high display qualities as well as the advantages of easy transportability and unbreakability. This is because the reactivity between the flexible substrate material of the liquid crystal cell and the liquid crystal material containing a tolan derivative is weak, thus limiting reactivity between the substrate material.

Figure 1:
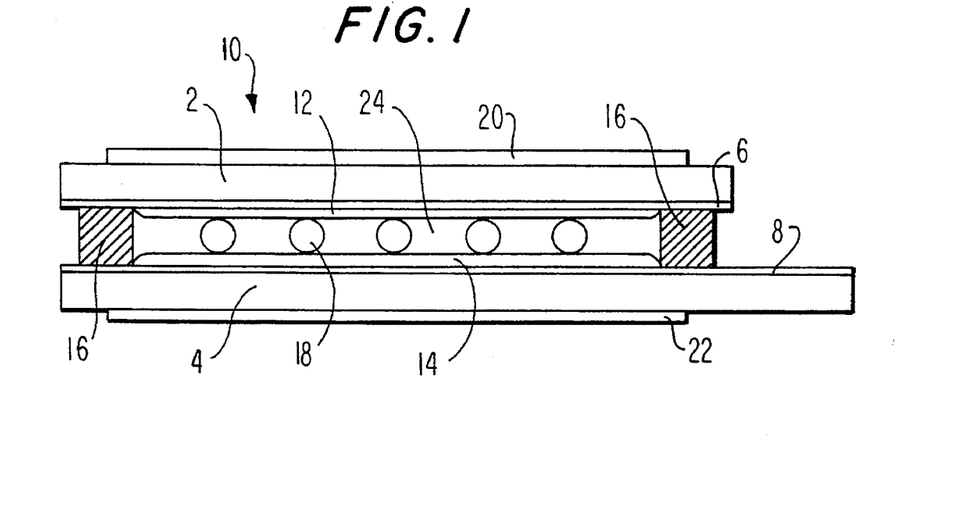
FIG. 1 is a sectional view of a liquid crystal cell constructed in accordance with the invention.

A liquid crystal display cell 10 constructed in accordance with the invention is shown in cross-section in FIG. 1. Liquid crystal cell 10 includes a flexible upper substrate 2 spaced apart from a flexible lower substrate 4. In an exemplary embodiment upper substrate 2 and lower substrate 4 are about 100 μm thick and have a flexible carbonate film as a base. The polycarbonate film has a gas barrier layer and a surface treated layer. An electrode pattern 6 is selectively disposed on an interior surface of upper substrate 2 and a cooperating electrode pattern 8 is disposed on an interior surface of lower substrate 4.

Electrodes 6 and 8 are preferably transparent conductive films such as ITO films. An orientation material such as polyimide or a similar material is applied over electrodes 6 and 8 to form film orientation (regulating) layers 12 and 14. Orientation film layers 12 and 14 are subjected to a rubbing process so that the liquid crystals will be oriented. A sealing member 16 is included around the periphery of the display to seal the space between flexible substrates 2 and 4. Sealing member 16 can be formed of an epoxy bonding agent so that upper substrate 2 and lower substrate 4 are polymerization bonded to each other. A plurality of spacers 18 are provided between the substrates. In an exemplary embodiment, spacers 18 are in the form of plastic beads.

An upper polarizing plate 20 is disposed on the outer surface of upper substrate 2 and a lower polarizing plate 22 is disposed on the outer surface of lower substrate 4. A liquid crystal composition 24 is disposed in the sealed space between substrates 2 and 4, thus forming a liquid crystal cell.

One example of a liquid crystal cell 10 is an STN-type cell having a liquid crystal layer with a twist angle of 210° to 240° and a value of Δn×d of about 0.8 to 0.9 μm, wherein Δn is the optical anisotropy and d is the thickness of the liquid crystal layer. Liquid crystal cell 10 may also be a reflection-type liquid crystal cell in which a reflecting plate is disposed below lower polarizing plate 22. The liquid crystal cell can also be a transparent type cell in which a back light is disposed below lower polarizing plate 22. Liquid crystal cells of this invention are not limited to STN-type cells. The present invention can also be applied to a black and white display-type liquid crystal display device as disclosed in Japanese Patent Publication No. 3-50249 and U.S. Pat. Nos. 4,844,569 and 5,212,819, the contents of which are incorporated herein by reference.

Although polycarbonate can be used as a material for the flexible substrate for a liquid crystal cell, other polymers are also suitable. For example, flexible substrates can also be formed of polyallylate, polyethersulfon (PES), polyethylene terephthalate (PET) and polyimide. In addition to organic films, plastic plates such as those approximately 0.3 mm thick can be used as the flexible substrate for the liquid crystal cell.

Liquid crystal cells shown in FIG. 1, were assembled in order to compare the performance of the liquid crystal cell of the present invention with liquid crystal cells employing glass substrates. A phenylcyclohexane (PCH-type) or biphenyl-type liquid crystal material are generally used in liquid crystal cells having glass substrates. Ester compounds and liquid crystal element compositions containing an ester compound and tolan derivatives (hereinafter also referred to as "an ester-type liquid crystal material" and "tolan-type liquid crystal material, respectively") are considered to have poor reliability in liquid crystal cells having glass substrates. PCH or biphenyl liquid crystal materials were added to liquid crystal compositions and sealed into a liquid crystal cell of the present invention containing flexible substrates. The same materials were also sealed into liquid crystal cells having glass substrates. For comparison, ester-type and tolan-type liquid crystal materials were added to a liquid crystal composition and were sealed into liquid crystal cells of the present invention and into liquid crystal cells having glass substrates. An environmental resistance test was conducted and data was collected for the two types of liquid crystal cells, one type having glass substrates, the other having flexible substrates. The comparative test results are shown in FIGS. 7 and 8, and the compositions of the PCH-type, biphenyl-type, ester-type and tolan-type liquid crystal materials are shown below.

|  | (mixture ratio) |
| --- | --- |
| PCH type | |
|  | 30 wt % |
|  | 65 |
|  | 5 |
| Biphenyl type | |
|  | 30 |
|  | 65 |
|  | 5 |
| Ester type | |
|  | 30 |
|  | 70 |
| Tolan type | |
|  | 20 |
|  | 65 |
|  | 5 |
|  | 10 |

Figure 7:
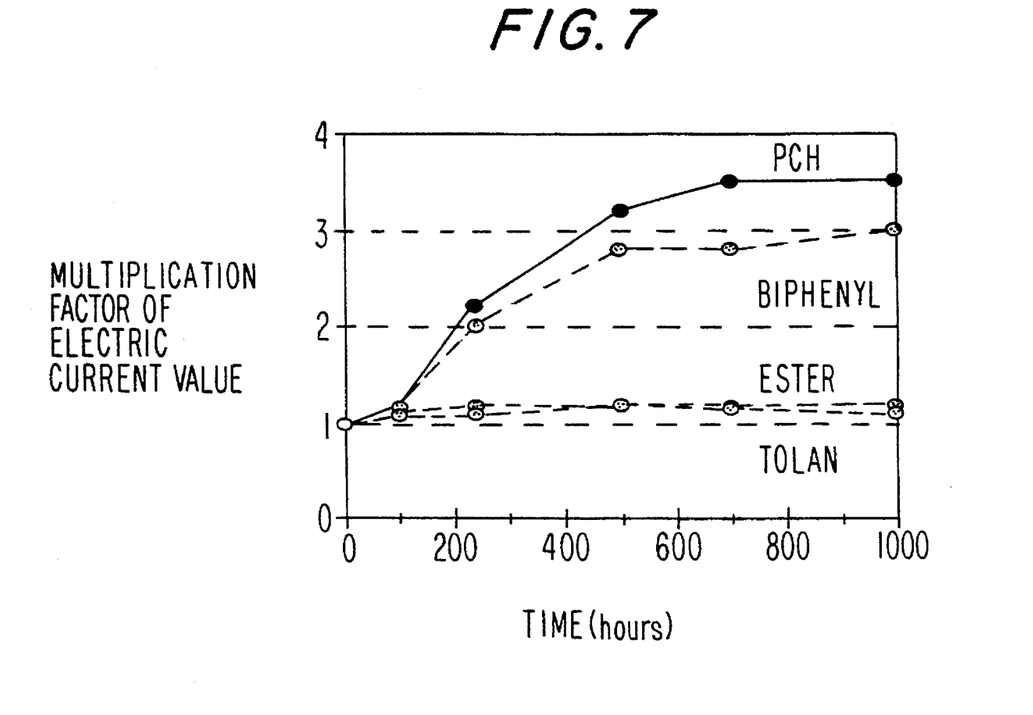
FIG. 7 is a graph depicting the environmental test results of a liquid crystal cell having a flexible substrate within which different liquid crystal compositions are disposed.
Figure 8:
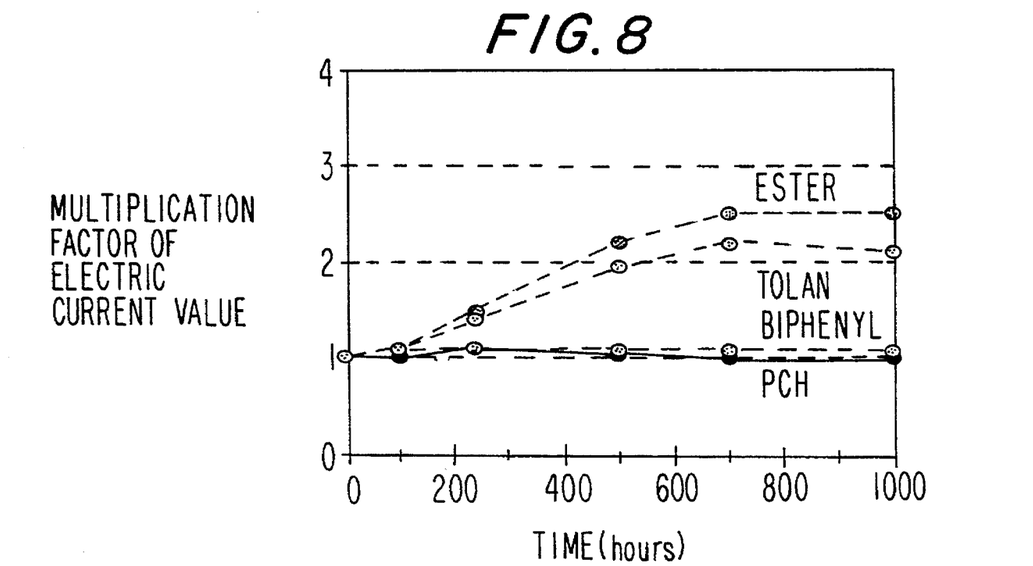
FIG. 8 is a graph depicting the environmental test results of a liquid crystal cell having conventional glass substrates within which different liquid crystal compositions are disposed.

FIG. 7 shows the test results of the different liquid crystal compositions in the liquid crystal cell having flexible substrates and FIG. 8 shows the test results of the liquid crystal materials in the liquid crystal cell having glass substrates. Although no reliability problems occurred with the phenyl-cyclohexane-type liquid crystal material or bi-phenyl-type liquid crystal material in the glass cell, the ester-type liquid crystal material and the tolan-type liquid crystal material in the glass cell showed poor reliability. The amount of electric current increased over time and display irregularities such as defective orientation were observed.

On the other hand, it was unexpectedly, observed that the liquid crystal compositions in the liquid crystal cell having flexible substrates showed tendencies totally opposite to those of the same materials in the glass cell. That is, the PCH-type liquid crystal material and the biphenyl-type liquid crystal material disposed within the liquid crystal cell having flexible substrates showed signs of poor reliability. The amount of electric current increased over time and display irregularities such as defective orientation were observed. In contrast, the liquid crystal cell having flexible substrates containing the ester liquid crystal material and the tolan liquid crystal material showed almost no increase in the amount of electric current and no defective orientation was observed. Thus, the PCH-type liquid crystal material and bi-phenyl-type liquid crystal material which performed well within the liquid crystal cell having glass substrates performed poorly in the liquid crystal cell having flexible substrates. The ester-type and tolan-type liquid crystal materials which performed poorly in the liquid crystal cell having glass substrates performed well in the liquid crystal cell having flexible substrates.

It was concluded that a significant factor influencing reliability of the liquid crystal display device is related to the problem of reactivity between the substrate material (i.e., glass substrate or flexible substrate) and the liquid crystal material. That is, the surface activity and affinity between the PCH and biphenyl-type liquid crystal materials and the flexible substrate is higher than the surface activity and affinity between the PCH and biphenyl liquid crystal materials and the glass substrate. This high reactivity between the flexible substrate and the PCH/biphenyl-type liquid crystal material causes poor performance of the liquid crystal cell. However, the surface activity between the flexible substrate and the ester and tolan liquid crystal materials is low. Unlike the case of glass substrates, no alkali ions or sodium is present so that it is difficult for reaction to take place, making the performance of these liquid crystal compositions in the liquid crystal cell having the flexible substrate more reliable.

On the basis of the above described results shown in FIGS. 7 and 8, it was found that the experience, know-how and knowledge about the glass cell, which has been accumulated over a long period of time, is not applicable to liquid crystal cells having flexible substrates. In the case of employing a liquid crystal cell having a flexible substrate, the composition of the liquid material is critical to the performance of the liquid crystal cell. Therefore, it is important to select a liquid crystal material specifically suitable for the liquid crystal cell having flexible substrates. Additionally, it was found that the reliability of a liquid crystal cell having flexible substrates is greatly enhanced by disposing an ester-type liquid crystal material and a tolan-type liquid crystal material within the flexible substrates. The ester-type liquid crystal material that is added to a liquid crystal composition along with the tolan material can be either an ester compound composition of a cyclohexane carboxylic acid phenyl ester having negative (n-type) induced anisotropy or a benzoic acid phenyl ester having positive (p-type) induced anisotropy or both n-type and p-type ester compounds can be added along with the tolan-type liquid crystal material to a liquid crystal composition.

The following examples are set forth below by way of illustration to show a liquid crystal cell of the present invention having a flexible substrate and high display quality. They are set forth for purposes of illustration only, and are not intended to be construed in a limiting sense.

EXAMPLE 1

A liquid crystal composition having the composition shown in Table 1 was sealed into the above-described liquid crystal cell, and was allowed to stand at a high temperature of 90° C. to conduct an environmental resistance test.

TABLE 1

| Composition | Mixture Ratio |
|---|---|
| C$_3$H$_7$—(H)—COO—(O)—OC$_2$H$_5$ | 7 Wt. % |
| C$_3$H$_7$—(H)—COO—(O)—OC$_4$H$_9$ | 17 Wt. % |
| C$_4$H$_9$—(H)—COO—(O)—OCH$_3$ | 13 Wt. % |
| C$_4$H$_9$—(H)—COO—(O)—OC$_2$H$_5$ | 13 Wt. % |
| C$_5$H$_{11}$—(H)—COO—(O)—OCH$_3$ | 15 Wt. % |
| C$_3$H$_7$—(H)—C≡C—(O with F,F)—CN | 10 Wt. % |
| C$_4$H$_9$—(H)—C≡C—(O with F,F)—CN | 10 Wt. % |
| C$_3$H$_7$—(H)—(O)—(O)—CH$_2$OCH$_3$ | 5 Wt. % |
| C$_5$H$_{11}$—(H)—(O)—(O)—(H)—CH$_2$OCH$_3$ | 10 Wt. % |

Figure 2:
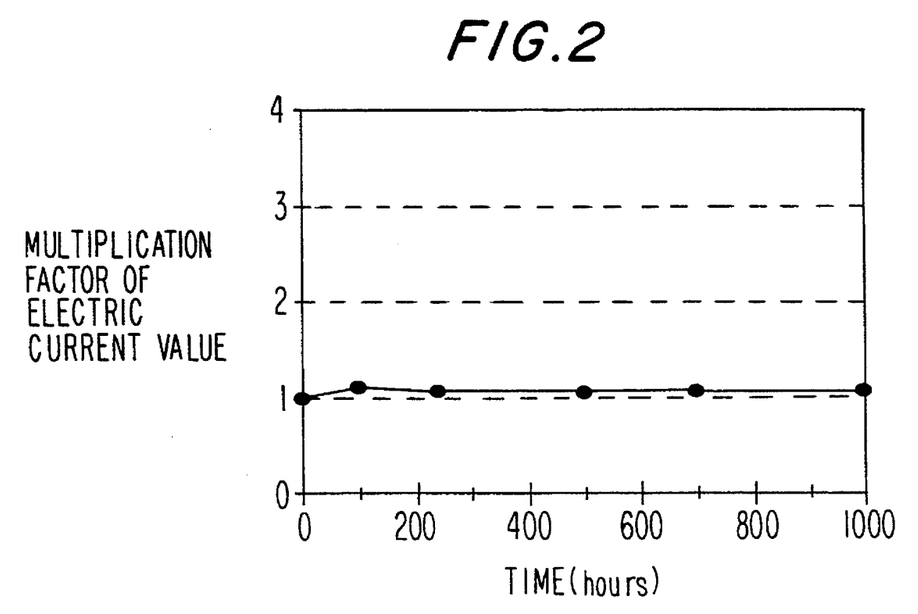
FIG. 2 is a graph depicting the results of an environmental resistance test conducted upon a flexible substrate liquid crystal cell having a liquid crystal composition including tolan derivatives and ester compounds in accordance with the invention.

The results of the environmental resistance test are shown in FIG. 2. In FIG. 2, the horizontal axis indicates the amount of time for which the liquid crystal cell was allowed to stand at a high temperature of 90° C. The vertical axis indicates an increase multiplication factor of the electric current value with respect to the initial current value. It can be seen from FIG. 2 that almost no increase in the amount of electric current was observed even if a left-as-it-is test at a temperature of 90° C. for 1,000 hours was conducted, and no defective orientation occurred at all. In addition, the reliability of the PFP flexible substrate cell was considerably better than that of a conventional glass substrate liquid crystal cell. Therefore, the selection of these liquid crystal materials for the PFP cell enables the reliability of the liquid crystal display to be improved considerably. In addition, LCD's formed in accordance with the invention have the advantage that it is possible to suppress an increase in the amount of electric current without changing at all the existing materials and conventional processes.

Materials other than a compound having an ester compound and the tolan derivatives are not limited to materials having the skeleton structure described in table 1, and the advantages of a liquid crystal material which is generally used are not limited to those described above.

There is no limitation regarding the mixture ratio of the compositions if the mixture ratio is in a range which does not deteriorate the electro-optic characteristics. It is preferable that the ratio of the n-type ester material be 50 to 80 wt. % and, preferably, 60 to 65 wt. %. Further, to improve the reliability under the condition where the voltage is decreased considerably, 2 to 25 wt. % of tolan derivatives and, more preferably, 6–20 wt. % and, more preferably 10 wt. % or less thereof should preferably be mixed as required. When the tolan derivatives exceed 25 wt. %, the liquid crystal is undesirably precipitated when a low-temperature test is conducted in which the liquid crystal cell is allowed to stand in a low-temperature environment of −30° C. in a liquid crystal composition state.

EXAMPLE 2

A liquid crystal composition having the composition shown in Table 2 was sealed into the above-described liquid crystal cell, and the same environmental resistance test conducted in Example 1 was conducted in this Example.

TABLE 2

| Composition | Mixture Ratio |
|---|---|
| C$_3$H$_7$—(H)—COO—(O)—OC$_2$H$_5$ | 6 Wt. % |
| C$_3$H$_7$—(H)—COO—(O)—OC$_4$H$_9$ | 16 Wt. % |
| C$_4$H$_9$—(H)—COO—(O)—OCH$_3$ | 12 Wt. % |
| C$_4$H$_9$—(H)—COO—(O)—OC$_2$H$_5$ | 13 Wt. % |
| C$_5$H$_{11}$—(H)—COO—(O)—OCH$_3$ | 14 Wt. % |
| C$_2$H$_5$—(O)—COO—(O)—CN | 9 Wt. % |
| C$_4$H$_9$—(O)—COO—(O)—CN | 6 Wt. % |
| C$_3$H$_7$—(H)—C≡C—(O with F,F)—CN | 3 Wt. % |
| C$_4$H$_9$—(H)—C≡C—(O with F,F)—CN | 3 Wt. % |
| C$_3$H$_7$—(H)—(O)—(O)—CH$_2$OCH$_3$ | 4 Wt. % |
| C$_5$H$_{11}$—(H)—(O)—(O)—CH$_2$OCH$_3$ | 4 Wt. % |
| C$_5$H$_{11}$—(H)—(O)—(O)—(H)—CH$_2$OCH$_3$ | 10 Wt. % |

Figure 3:
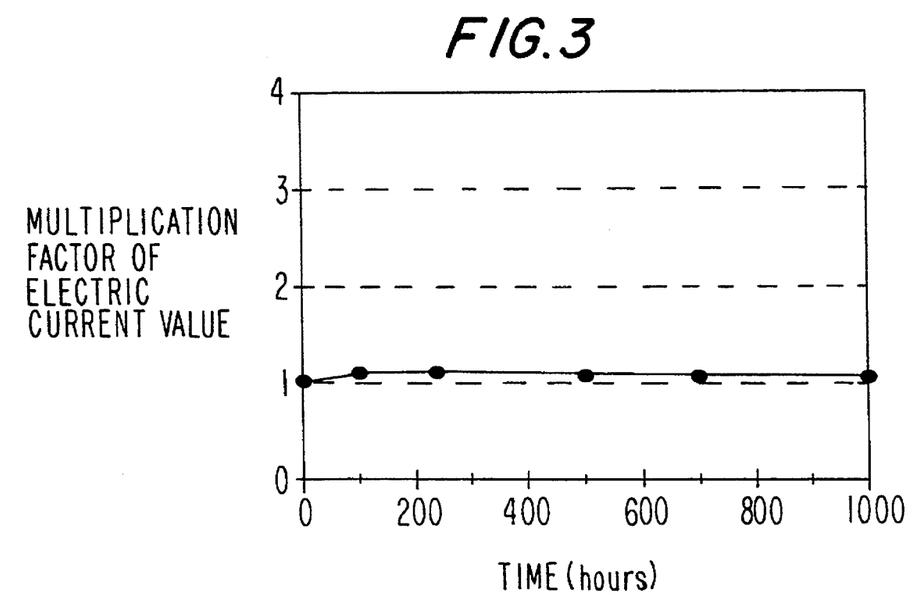
FIG. 3 is a graph depicting the results of an environmental resistance test conducted on a flexible substrate liquid crystal cell having another liquid crystal composition including tolan derivatives and ester compounds.

The results thereof are shown in FIG. 3. Even after the liquid crystal cell was left at 90° C. for 1,000 hours, as in the case of Example 1, no increase in the amount of electric current and no defective orientation were observed. Thus, reliability was considerably better than for a conventional cell. Therefore, it is possible to improve the reliability of the liquid crystal element considerably by selecting these above materials for the PFP. In addition, there is the advantage that it is possible to suppress an increase in the amount of electric current without changing at all the existing materials and the conventional processes.

Regarding materials other than n-type and p-type compounds having ester bonding and tolan derivatives in Table 2, the advantages thereof are not limited to those described above even if generally-used liquid crystal materials, in addition to those having the skeleton structure described in Table 2, are used.

The mixture ratio of the compositions is not limited if it is within a range which does not deteriorate the electro-optic characteristics. However, it is preferable that the mixture ratio of the n-type ester material be 50 to 80 wt. % and, more preferably, 60 to 65 wt. %. Further, it is preferable that 2 to 25 wt. % and, more preferably, 6–20 wt. %, and more preferably, 10 wt. % or less of p-type tolan derivatives be mixed as necessary in order to improve the reliability under the condition where the voltage is greatly decreased. If the tolan derivatives exceed 25 wt. %, the liquid crystals are undesirably precipitated when a low temperature test is conducted in which it is left in a liquid crystal composition state in a low temperature environment of −30° C.

In addition, to improve the compatibility at low temperatures and expand the range in which An is adjusted, it is preferable that a p-type ester compound be mixed in the range of a mixture ratio of 5 to 30 wt. % and, more preferably, 10 to 20 wt. %, and more preferably, 15 wt. % or less.

EXAMPLE 3

The composition of the liquid crystal shown in Table 3, below, was sealed into the above-described liquid crystal element to conduct the same environmental resistance test as conducted in Example 1;

TABLE 3

| Composition | Mixture Ratio |
| --- | --- |
| $C_3H_7$—(H)—COO—(O)—$OC_2H_5$ | 6 Wt. % |
| $C_3H_7$—(H)—COO—(O)—$OC_4H_9$ | 17 Wt. % |
| $C_4H_9$—(H)—COO—(O)—$OCH_3$ | 13 Wt. % |
| $C_4H_9$—(H)—COO—(O)—$OC_2H_5$ | 13 Wt. % |
| $C_5H_{11}$—(H)—COO—(O)—$OCH_3$ | 14 Wt. % |
| $C_2H_5$—(O)—COO—(O)—CN | 5 Wt. % |
| $C_3H_7$—(H)—C≡C—(O, F, F)—CN | 7 Wt. % |
| $C_4H_9$—(H)—C≡C—(O, F, F)—CN | 7 Wt. % |

TABLE 3-continued

| Composition | Mixture Ratio |
| --- | --- |
| $C_3H_7$—(H)—(O)—(O)—$CH_2OCH_3$ | 4 Wt. % |
| $C_5H_{11}$—(H)—(O)—(O)—$CH_2OCH_3$ | 4 Wt. % |
| $C_5H_{11}$—(H)—(O)—(O)—(H)—$CH_2OCH_3$ | 10 Wt. % |

Figure 4:
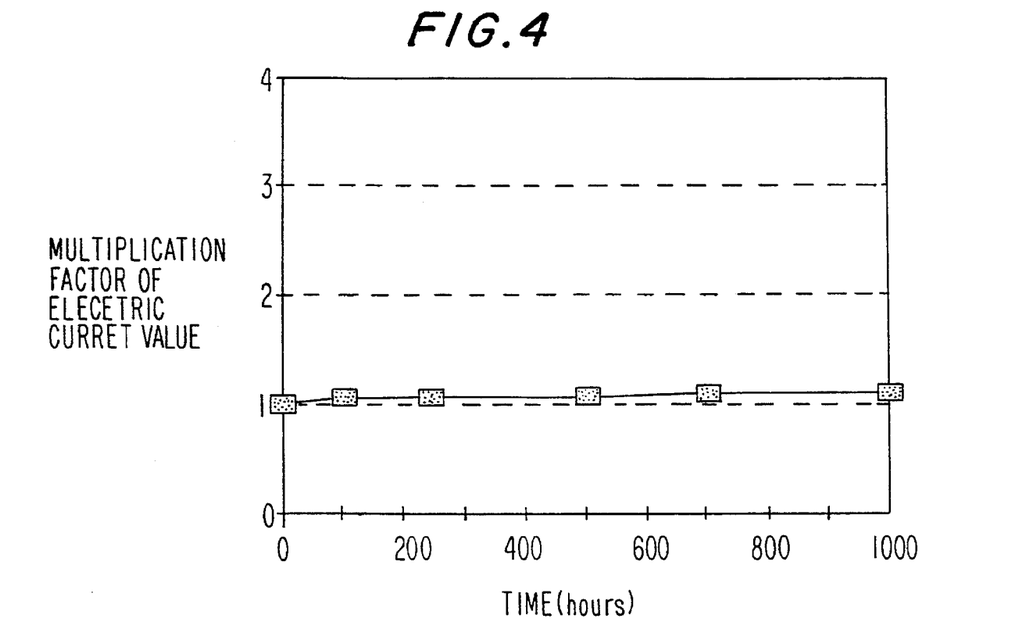
FIG. 4 is a graph depicting the results of an environmental resistance test on a flexible substrate liquid crystal cell having another liquid crystal composition including tolan derivatives and ester compounds.

The results thereof are shown in FIG. 4. In the same manner as in Example 1, even after the liquid crystal element was left at 90° C. for 1,000 hours, no increase in the amount of electric current and no defective orientation were observed, and reliability was far better than the conventional liquid crystal element. Therefore, by selecting these materials for PFP, it is possible to considerably increase the reliability of the liquid crystal element. In addition, there is the advantage that an increase in the amount of electric current can be suppressed without changing the existing materials and the conventional processes in any way.

Materials in the table other than the compound having n-type and p-type ester bonding and tolan derivatives are not limited to materials having the skeleton structure described in the table; even if generally-used liquid crystal materials are used, the advantages thereof are not limited to those described above.

There is no limitation regarding the mixture ratio of the compositions if it is within a range which does not worsen the electro-optic characteristics. However, the mixture ratio of n-type ester material is preferably 50 to 80 wt. % and, more preferably, 60 to 65 wt. %. Further, to improve reliability under the condition where the voltage is considerably decreased, 2 to 25 wt. % and, more preferably, 6–20 wt. % and, more preferably 10 wt. % or less, of p-type tolan derivatives should be added as necessary. If the tolan derivatives exceed 25 wt. %, the liquid crystals undesirably precipitate when a low temperature test is conducted in which the derivative are loft in a liquid crystal composition state in a low temperature environment of −30° C.

In addition, it is preferable that the ratio of a p-type ester compound be added in the range of 5 to 30 wt. % and, more preferably, 10 to 20 wt. % and, more preferably 15 wt. % or less in order to improve the compatibility at low temperatures and expand the range in which An is adjusted.

EXAMPLE 4

Figure 5:
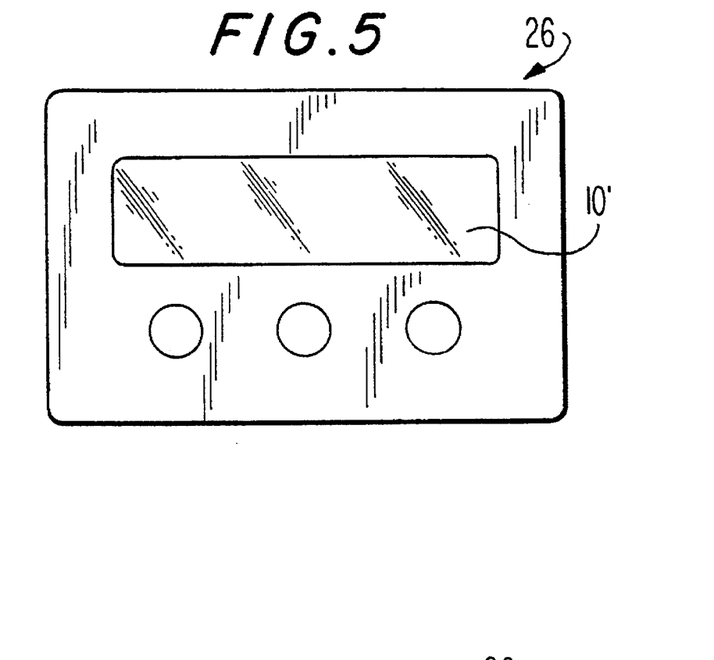
FIG. 5 shows a liquid crystal display cell of the invention installed within an electronic pager.

A liquid crystal cell was used as a liquid crystal display element 10' for a pager 26 shown in FIG. 5. Display element 10' for pager 5 is thinner and lighter than a conventional liquid crystal element formed of glass and has excellent resistance to impact. More specifically, it is resistant to stresses occurring when it is carried in the pocket of the user. Unlike a glass cell, even if it were dropped by mistake, the liquid crystal element is less likely to break. It is possible to obtain a more reliable pager because there is no defective display caused by breakage or cracks, which has been problematical in the prior art. In addition, reliability with respect to the use and storage at high temperatures was considerably increased compared with the conventional product. Thus, a pager capable of being satisfactorily used outdoors and having high display quality could be obtained.

EXAMPLE 5

Figure 6:
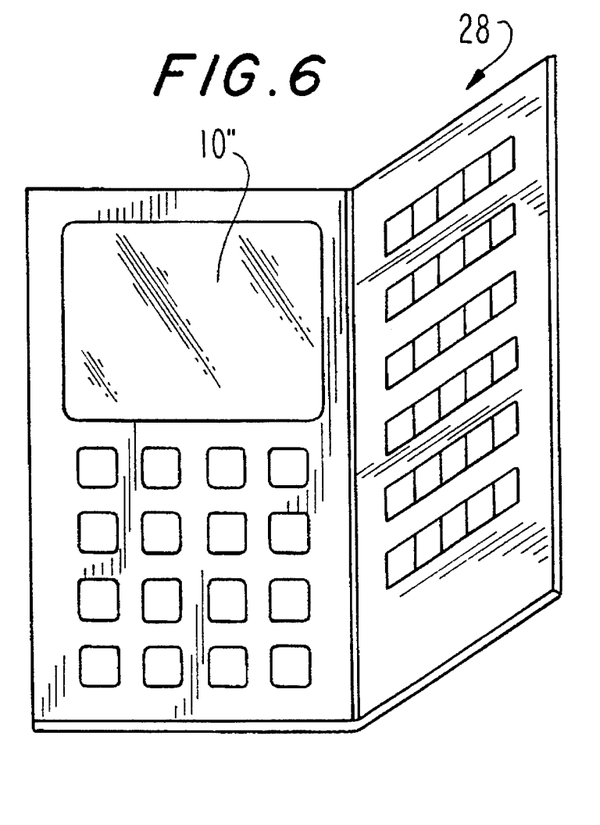
FIG. 6 shows a liquid crystal display cell of the invention installed within an electronic calculator.

Liquid crystal element 10" was installed in an electronic pocket notebook 28 as shown in FIG. 6. Electronic pocket notebook 28 can thereby be thinner and lighter than if liquid crystal element 10" were formed of glass. Notebook 28 has excellent resistance to environment and impact, as in Example 4. More specifically, electronic notebook 28 is strong against stresses occurring when it is carried in the pocket of the user. Even if it were dropped by mistake, unlike the glass cell, the liquid crystal element is less likely to be broken. Therefore, there is no defective display caused by breakage or cracks, which has been problematical in the prior art, making it possible to obtain a more reliable electronic pocket notebook. Also, since the thickness of the substrate is 1/5 to 1/10 that of the glass substrate, particularly when it is used as a reflection type LCD equipped with a reflecting plate on the rear surface of the liquid crystal element as in this example, the parallax between the display section and the reflection section becomes small, preventing a double image in the display depending upon the parallax. Thus, an electronic apparatus having a great parallax and high display quality could be obtained. In addition, reliability with respect to the use and storage at high temperatures was considerably better than a conventional product, and an electronic pocket notebook having excellent resistance to the environment could be obtained. Thus, it can be stably used outdoors for a long period of time.

Although FIGS. 5 and 6 show embodiments of a portable pager and an electronic pocket notebook using the liquid crystal cell of the present invention having flexible substrates, in addition to the above-described embodiments, it is possible to provide an excellent electronic apparatus by installing the liquid crystal cell of the present invention as a liquid crystal display device in various other electronic apparati such as portable telephones, personal digital assistance (PDA) devices, or personal computers.

Since a liquid crystal composition containing at least an ester compound whose dielectric constant anisotropy is negative and a tolan derivative whose induction anisotropy is positive is sealed into the liquid crystal element of the present invention, an increase in the amount of electric current can be prevented in a condition in which the liquid crystal element is left at high temperatures. Therefore, resistance to the environment is considerably improved for the liquid crystal cell having a flexible substrate. The liquid crystal element has the advantage that the driving voltage is decreased and response speed is improved. Further, in addition to ensuring reliability, the driving voltage and the range in which An can be adjusted is expanded by mixing an ester compound whose induced anisotropy is negative with the above-described liquid crystal composition. Therefore, since it is possible to select a liquid crystal composition according to the specifications, a wider selection of materials is possible.

Since the electronic apparatus of the present invention has installed therein the liquid crystal element having a flexible substrate, as described above, it has excellent characteristics which the conventional glass cell apparatus does not have, for example, excellent resistance to impact and the capability of being formed thinly and lightly.

It will thus be seen that the objects set forth above, among those made apparent from the preceding description, are efficiently attained and, since certain changes may be made in carrying out the above process, in the described product, and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. A liquid crystal display cell, comprising:

a pair of spaced apart opposed substrates, at least one of which is a flexible substrate formed of organic material;

a liquid crystal composition including a liquid crystal material sealed in the space between the flexible substrates, the liquid crystal material including a tolan derivative represented by the general formula:

where R is a straight chain alkyl group having from 1 to carbon atoms; and an electrode pattern supported by the interior surface of the opposed flexible substrates.

2. The liquid crystal display cell of claim 1, wherein the liquid crystal composition includes at least one of an ester compound of a cyclohexane carboxylic acid phenyl ester having negative (n-type) induced anisotropy represented by the general formula:

where R and R' are straight chain alkyl groups having from 1 to 10 carbon atoms, and a benzoic acid phenyl ester having positive (p-type) induced anisotropy represented by the general formula:

where R is a straight chain alkyl group having from 1 to 10 carbon atoms.

3. The liquid crystal display cell of claim 2, wherein the organic material includes polymer material.

4. The liquid crystal display cell of claim 2, wherein the flexible substrate is a polycarbonate film.

5. The liquid crystal display cell of claim 2, wherein the flexible substrate is selected from the group consisting of polyallylate, polyethersulfon, polyethylene terephthalate and polyimide.

6. The liquid crystal display cell of claim 2, wherein the tolan derivative is 2 to 25 wt. % of the total liquid crystal composition.

7. The liquid crystal display cell of claim 2, wherein the tolan derivative is 6 to 20 wt. % of the total liquid crystal composition.

8. The liquid crystal display cell of claim 2, wherein the tolan derivative is less than 10% of the total liquid crystal composition.

9. The liquid crystal cell of claim 2, wherein the cyclohexane carboxylic acid phenyl ester is 50 to 80 wt. % and the benzoic acid phenyl ester is 5 to 30 wt. % of the total liquid crystal composition.

10. The liquid crystal cell of claim 2, wherein the cyclohexane carboxylic acid phenyl ester is 60 to 65 wt. % and the benzoic acid phenyl ester is 5 to 15 wt. % of the total liquid crystal composition.

11. The liquid crystal cell of claim 2, wherein the benzoic acid phenyl ester is 0 to 15 wt. % of the total liquid crystal composition.

12. The liquid crystal display cell of claim 1, wherein the liquid crystal composition includes an ester compound of a cyclohexane carboxylic acid phenyl ester having negative (n-type) induced anisotropy represented by the general formula:

where R and R' are straight chain alkyl groups having from 1 to 10 carbon atoms.

13. The liquid crystal display cell of claim 12, wherein the cyclohexane carboxylic acid phenyl is 50 to 80 wt. % of the total liquid crystal composition.

14. The liquid crystal display cell of claim 12, wherein the cyclohexane carboxylic acid phenyl is 60 to 65 wt. % of the total liquid crystal composition.

15. The liquid crystal display cell of claim 1, wherein the liquid crystal composition includes a benzoic acid phenyl ester having positive (p-type) induced anisotropy represented by the general formula:

where R is a straight chain alkyl group having from 1 to 10 carbon atoms.

16. The liquid crystal display cell of claim 15, wherein the benzoic acid phenyl ester is 5 to 30 wt. % of the total liquid crystal composition.

17. The liquid crystal display cell of claim 15, wherein the benzoic acid phenyl ester is 5 to 15 wt. % of the total liquid crystal composition.

18. The liquid crystal display cell of claim 15, wherein the benzoic acid phenyl ester is 0 to 15 wt. % of the total liquid crystal composition.

19. An electronic apparatus having installed therein a liquid crystal display cell comprising:

a pair of spaced apart opposed flexible substrates, at least one of which is formed of organic material;

a liquid crystal composition including a liquid crystal material sealed in the space between the flexible substrates the liquid crystal material including a tolan derivative represented by the general formula:

where R is a straight chain alkyl group having from 1 to 20 carbon atoms; and an electrode pattern supported by the interior surface of the opposed flexible substrates.

* * * * *